US011972585B2

United States Patent
Chang et al.

(10) Patent No.: US 11,972,585 B2
(45) Date of Patent: Apr. 30, 2024

(54) DENSE BODY MARKER ESTIMATION FROM CAMERA DATA FOR PATIENT POSITIONING IN MEDICAL IMAGING

(71) Applicant: Siemens Healthineers AG, Forchheim (DE)

(72) Inventors: Yao-Jen Chang, Princeton, NJ (US); Jiangping Wang, Carteret, NJ (US); Vivek Singh, Princeton, NJ (US); Ruhan Sa, Monmouth Junction, NJ (US); Ankur Kapoor, Plainsboro, NJ (US); Andreas Wimmer, Forchheim (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/348,407

(22) Filed: Jul. 7, 2023

(65) Prior Publication Data
US 2023/0368404 A1 Nov. 16, 2023

Related U.S. Application Data

(62) Division of application No. 16/269,732, filed on Feb. 7, 2019, now Pat. No. 11,748,899.

(51) Int. Cl.
*A61B 5/00* (2006.01)
*A61B 5/01* (2006.01)
(Continued)

(52) U.S. Cl.
CPC .............. *G06T 7/40* (2013.01); *A61B 5/0077* (2013.01); *A61B 5/015* (2013.01); *A61B 5/107* (2013.01);
(Continued)

(58) Field of Classification Search
CPC ....... A61B 5/0077; A61B 5/015; A61B 5/107; A61B 5/704; A61B 5/7264; A61B 5/7267;
(Continued)

(56) References Cited

U.S. PATENT DOCUMENTS

| 10,783,655 B2 | 9/2020 | Zhao et al. |
| 2016/0306924 A1 | 1/2016 | Singh et al. |

(Continued)

OTHER PUBLICATIONS

Choy, Christopher B., Danfei Xu, JunYoung Gwak, Kevin Chen, and Silvio Savarese. "3d-r2n2: A unified approach for single and multi-view 3d object reconstruction." In European conference on computer vision, pp. 1-17. Springer, Cham, 2016.
(Continued)

*Primary Examiner* — Joel F Brutus (57) ABSTRACT

Machine learning is used to train a network to estimate a three-dimensional (3D) body surface and body regions of a patient from surface images of the patient. The estimated 3D body surface of the patient is used to determine an isocenter of the patient. The estimated body regions are used to generate heatmaps representing visible body region boundaries and unseen body region boundaries of the patient. The estimation of 3D body surfaces, the determined patient isocenter, and the estimated body region boundaries may assist in planning a medical scan, including automatic patient positioning.

4 Claims, 7 Drawing Sheets

(51) Int. Cl.
  *A61B 5/107* (2006.01)
  *G06T 7/40* (2017.01)
  *G06T 7/66* (2017.01)

(52) U.S. Cl.
  CPC ............ *A61B 5/704* (2013.01); *A61B 5/7264* (2013.01); *A61B 5/7267* (2013.01); *G06T 7/66* (2017.01); *G06T 2207/10024* (2013.01); *G06T 2207/10028* (2013.01); *G06T 2207/10048* (2013.01); *G06T 2207/20081* (2013.01); *G06T 2207/20084* (2013.01); *G06T 2207/30004* (2013.01)

(58) Field of Classification Search
  CPC . G06T 2207/10024; G06T 2207/10028; G06T 2207/10048; G06T 2207/20081; G06T 2207/20084
  See application file for complete search history.

(56) References Cited

U.S. PATENT DOCUMENTS

| | | | |
|---|---|---|---|
| 2017/0035374 A1 | 2/2017 | Schafer et al. | |
| 2017/0311921 A1 | 11/2017 | Feuerlein et al. | |
| 2017/0354385 A1 | 12/2017 | Lerch | |
| 2018/0046875 A1 | 2/2018 | Caluser | |
| 2018/0049669 A1* | 2/2018 | Vu | A61B 5/0507 |
| 2018/0228460 A1 | 8/2018 | Singh et al. | |
| 2018/0300621 A1* | 10/2018 | Shah | G06N 3/044 |
| 2019/0220986 A1 | 7/2019 | Margo et al. | |

OTHER PUBLICATIONS

Güler, Riza Alp, George Trigeorgis, Epameinondas Antonakos, Patrick Snape, Stefanos Zafeiriou, and Lasonas Kokkinos. "DenseReg: Fully Convolutional Dense Shape Regression In-the-Wild." In CVPR, vol. 2, p. 5. 2017. 1-11.

Güler, Rza Alp, Natalia Neverova, and Iasonas Kokkinos. "Densepose: Dense Human Pose Estimation in the Wild." arXiv preprint arXiv:1802.00434 (2018). 1-12.

J. Song, L. Wang, L. Gool and O. Hilliges. "Thin-slicing network: a deep structured model for pose estimation in videos." In Proceedings of the IEEE Conference on Computer Vision and Pattern Recognition, 2017. 1-10.

Jégou, Simon, Michal Drozdzal, David Vazquez, Adriana Romero, and Yoshua Bengio. "The One Hundred Layers Tiramisu: Fully Convolutional DenseNets for Semantic Segmentation." In Computer Vision and Pattern Recognition Workshops (CVPRW), 2017 IEEE Conference. 1-9.

Newell, Alejandro, Kaiyu Yang, and Jia Deng. "Stacked Hourglass Networks for Human Pose Estimation." In European Conference on Computer Vision, Springer International Publishing, 2016. 1-17.

Qian Chen, Haiyuan Wu, and Toshikazu Wada, "Camera Calibration with Two Arbitrary Coplanar Circles", Proceedings of ECCV 2004. 1-12.

S. Wei, V. Ramakrishna, T. Kanade and Y. Sheikh. "Convolutional Pose Machines." In Proceedings of the IEEE Conference on Computer Vision and Pattern Recognition, 2016.

Liu Dezhi et al:, "Real-time 3D image guided patient positioning in radiation therapy", Proc. of SPIE, vol. 605613, pp. 605613-1-605613-7, XP040217457 / Jan. 1, 2006.

Singh Vivek et al:, "DARWIN: Deformable Patient Avatar Representation With Deep Image Network", 12th European Conference on Computer Vision, ECCV 12, Springer Berlin Heidelberg, pp. 497-504, XP047528084, ISSN: 0302-9743, ISBN: 978-3-642-36948-3 / Apr. 9, 2017.

Yadati Pramod et al:, "Multiscale Two-view stereo using Convolutional Neural Networks for Unrectified Images", 2017 Fifteenth IAPR International Conference on Machine Vision Applications (MVA), MVA Organization, pp. 346-349, XP 033126598, DOI: 10.23919/MVA.2017.7986872 / Aug. 5, 2017.

Anonymous: "Isocenter definition of isocenter by Medical dictionary"; Jan. 1, 2009 (Jan. 1, 2009); XP055936138 [retrieved on Jun. 28, 2022], 2 pages.

Wikipedia: "Isocenter"; Dec. 14, 2017 (Dec. 14, 2017); retrieved from "https://en.wikipedia.org/w/indes.php?title=Isocenter&oldid=815375635"; XP055936139; 1 page.

Wikipedia: "Point cloud."; Wikimedia Foundation; URL's: https://web.archive.org/web/20170711062354/; https://en.wikipedia.org/wiki/Point_cloud. (Year:2017).

* cited by examiner

DENSE BODY MARKER ESTIMATION FROM CAMERA DATA FOR PATIENT POSITIONING IN MEDICAL IMAGING

CROSS-REFERENCE TO RELATED APPLICATIONS

This application is a divisional of U.S. application Ser. No. 16/269,732, filed on Feb. 7, 2019, the contents of which are incorporated by reference.

TECHNICAL FIELD

The present teachings relate generally to the estimation of patient body surfaces from camera data, and more particularly to patient positioning during medical imaging.

BACKGROUND

Medical imaging techniques—including but not limited to computed tomography (CT), magnetic resonance (MR), positron emission tomography (PET), single photon emission computed tomography (SPECT) data, and the like—rely on proper patient positioning, which includes identifying a patient's position on a patient table of the medical imager and/or correcting for movement of the patient. In some cases, sensors, such as a camera, may be mounted to a medical imaging device to provide patient position and movement data during a medical imaging scan. The sensors, however, may be mounted to the medical imager in such a way that the sensors provide a limited field of view, which limits the use and analysis of such images during the medical imaging scans.

In addition, current systems require an operator to perform one or more adjustments to a moveable patient table, or bed, to properly position a patient prior to initiating a medical imaging scan. Improper positioning may lead to errors or artifacts in the medical image. The manual patient positioning process involving operator adjustments can be time consuming, costly, and require operators to spend time away from other tasks to perform such adjustments.

SUMMARY

The scope of the present invention is defined solely by the appended claims, and is not affected to any degree by the statements within this summary.

In accordance with the present teachings, an approach for estimating a three-dimensional (3D) body surface of a patient from data captured from a sensor (e.g., camera) in a clinical setting (e.g., a CT scanning room) is described. Machine learning is used to train a network to estimate body markers from surface data, such as surface images of the patient, and reconstruct the 3D body surface based on the estimated body markers. The 3D body surface reconstruction includes partitioning the surface images of the patient, assigning a classification to surface image pixels, and determining 3D surface coordinates for the surface image pixels. The estimated 3D body surface is used to determine an isocenter of the patient. The 3D body surface of the patient is estimated within the coordinate frame of the medical imaging scanner (e.g., CT scanner), and may be used in a variety of applications (e.g., including but not limited to automating the patient positioning process, avoiding positioning errors and increasing efficiency of usage of the scanner).

An approach for estimating body regions of a patient from data captured from a sensor in a clinical setting is also described. Machine learning is used to train a network to estimate body regions, or body region boundaries, of the patient (e.g., head, neck, shoulder, hip, groin, knee, ankle, etc.). Machine learning is also used to generate heatmaps (e.g., Gaussian heatmaps) that represent the visible and unseen body region boundaries of the patient.

In a first aspect, a method is provided for estimating a 3D body surface of a patient located on a moveable patient table in a medical imaging system. A sensor captures a sequence of surface images of the patient. A processor estimates the 3D body surface of the patient by a machine-learned network in response to input of the surface images to the machine-learned network. The processor determines an isocenter of the patient based on the estimated 3D body surface of the patient and based on a position of the moveable patient table. The processor positions the patient via the moveable patient table based on the determined isocenter of the patient.

In a second aspect, a medical imaging system is provided for estimating a 3D body surface of a patient. A sensor is configured to capture a sequence of surface images of the patient. A processor is configured to apply a machine-learned neural network to the sequence of surface images. The machine-learned neural network was trained to estimate the 3D body surface of the patient from the sequence of surface images. The processor is also configured to determine an isocenter of the patient based on the estimated 3D body surface of the patient. A moveable patient table is configured to automatically position the patient based on the determined isocenter of the patient and based on a position of the moveable patient table.

In a third aspect, a method is provided for estimating body regions of a patient located on a moveable patient table in a medical imaging system. A sensor captures a sequence of surface images of the patient. A processor estimates the body regions of the patient by a machine-learned network in response to input of the surface images to the machine-learned network. The processor also generates Gaussian heatmaps by the machine-learned network in response to input of the surface images to the machine-learned network. The Gaussian heatmaps represent visible and unseen body region boundaries of the patient along a longitudinal axis of the moveable patient table.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Embodiments disclosed herein address challenges associated with patient positioning and monitoring in medical imaging, such as computed tomography (CT), magnetic resonance (MR), positron emission tomography (PET), single photon emission computed tomography (SPECT), and the like. A sequence of two-dimensional (2D) images obtained from a sensor, such as a camera, mounted to or relative to an outer surface of an imaging device are used to automatically position a patient prior to initiating a medical imaging procedure and to monitor the patient movement during the procedure and re-position the patient, if necessary. Embodiments disclosed herein can be used in an automated workflow for patient scanning using CT, MR, PET or SPECT scanners. In the typical workflow for patient scanning using these types of scanners, the radiologist/ technician first roughly estimates the patient isocenter of the scan region by observing the patient contour from a profile viewpoint, and then aligns the estimated patient isocenter with the scanner gantry center, which is usually reflected by the laser projection. If the alignment is perfectly conducted, the best imaging quality will be achieved. However, the current alignment done by the radiologist/technician may be inaccurate and inconsistent.

Embodiments disclosed herein can be used to estimate a 3D body surface of the patient that will be further used to automatically determine the isocenter of the patient and scan region. Compared to the traditional workflow used by the radiologist/technician, this can provide a more accurate and consistent estimation of the isocenter, resulting in more diagnostically useful images. In addition, in the typical workflow for patient scanning using CT or PET scanners, for example, a topogram (x-ray) image is first generated with the scanner to help the radiologist determine the necessary scan region. Embodiments disclosed herein can be used to estimate a 3D body surface of the patient from surface images obtained using a sensor, such as a camera, and the 3D body surface of the patient can be used in place of the topogram to automatically determine the isocenter of the patient. This can provide a more accurate estimation of the scan range for an area to be scanned and decrease the patient's exposure to radiation. Embodiments disclosed herein can also be used to estimate body regions of a patient from a 2D or 3D camera stream having a limited field of view, which can be used for assisted patient positioning.

With the rapid development of sensing technology and artificial intelligence, 2D camera-assisted patient positioning is possible. In order to automate medical imaging workflows, such as a CT scanning workflow, it is desirable to center the patient to align with the CT isocenter. Embodiments disclosed herein provide for automatic patient positioning including centering by estimating body markers of a patient body from 2D video sequences. Body marker estimation maps human pixels of a Red-Green-Blue (RGB) image to a 3D surface of the human body. By estimating body markers of a patient body, image pixels are able to be associated to respective parts of a body surface, which allows for a 3D reconstruction and partitioning of a patient body for isocentering purposes. Embodiments disclosed herein also provide for camera assisted patient positioning by estimating body regions of a patient and generating heatmaps that represent visible and unseen body region boundaries of the patient.

In one embodiment, surface images of a patient lying on a patient table from a 2D video sequence captured by a 2D camera mounted on a scanner gantry are used to estimate dense body markers of the patient and reconstruct a 3D body surface of the patient by integrating temporal information into a dense body marker regression network. The obtained 3D surface, together with a patient table position, can be directly used to automatically determine, by regression, a patient isocenter for patient centering and positioning. Automatic patient isocentering and positioning utilizes state-of-the-art deep machine learning techniques, such as a fully convolutional network and/or Long Short-Term Memory (LSTM) units for recurrent body marker estimation and 3D surface reconstruction. The positioning by regression is particularly useful for handling instances of limited field of views from 2D cameras mounted on a scanner gantry. A 3D model of a patient body may be built using a Deformable patient Avatar Representation With deep Image Network ("DARWIN"), which is a method to estimate a detailed body surface mesh of a covered patient lying on a table or a bed from a single snap-shot of a range or depth sensor.

In another embodiment, surface images of a patient lying on a patient table from a 2D video sequence captured by a 2D camera mounted on a scanner gantry are used to estimate body regions of the patient and generate heatmaps, such as Gaussian heatmaps, that represent the visible and unseen body region boundaries of the patient along a longitudinal axis of the moveable patient table. The estimation of the body regions is performed by a machine-learned network, such as a fully convolutional network. The network detects visible body region boundaries of the patient from the sequence of surface images of the patient, extrapolates unseen body region boundaries of the patient based on the detected visible body region boundaries, aggregates, by a temporal module, the detected visible body region boundaries and the extrapolated unseen body region boundaries from the sequence of surface images, and determines the body regions of the patient based on the aggregated visible body region boundaries and the unseen body region boundaries.

It is to be understood that elements and features of the various representative embodiments described below may be combined in different ways to produce new embodiments that likewise fall within the scope of the present teachings.

Figure 1:
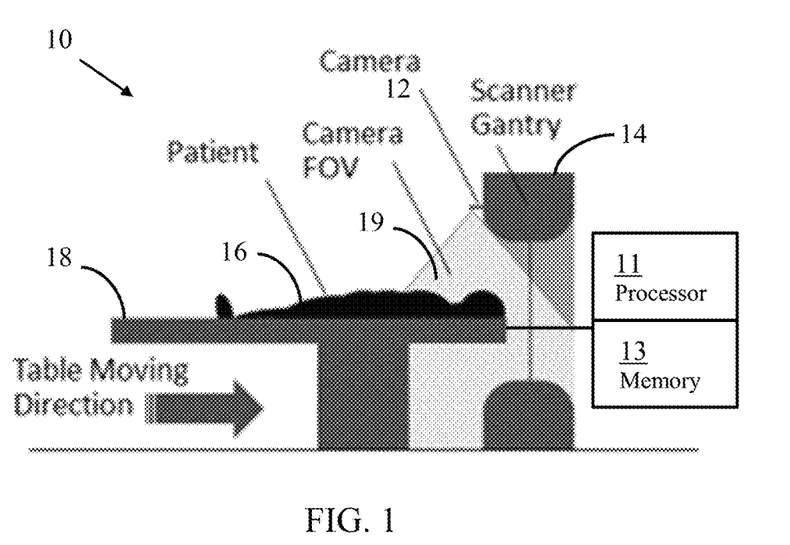
FIG. 1 illustrates an example setup of a sensor near a scanner gantry of a medical imaging system and one embodiment of a medical imaging system for estimating a 3D body surface of a patient.

By way of introduction, FIG. 1 shows the setup of a sensor 12 near a scanner gantry 14 of a medical imaging system 10. The sensor 12 is mounted to or relative to the gantry 14 such that a patient 16 lying on a patient table 18 in front of the scanner gantry 14 and/or partially inside the scanner gantry 14 can be monitored. Additional, different, or fewer components may be used. In one embodiment, the medical imaging system 10 may include an x-ray or optical topography system.

The sensor 12 may be a camera or cameras capturing surface images of the patient 16. The sensor 12 may also be multiple cameras capturing 2D images from different directions. The sensor may be a depth sensor, such as a 2.5D or RGBD sensor (e.g., Microsoft Kinect 2 or ASUS Xtion Pro), time-of-flight devices (e.g., Creative TOF cameras), or a combination thereof. The sensor may be a camera or cameras capturing a grid projected onto the patient. The sensor may be multiple cameras capturing 2D images from different directions. Other optical or non-ionizing sensors 12 may be used. In one embodiment, the sensor may be an optical camera. In another embodiment, the sensor 12 may be mounted on a different component of the medical imaging system 10. In yet another embodiment, the sensor 12 may be mounted to a component of the clinical setting other than the medical imaging system 10.

A patient 16 lying on the patient table 18 will be moved in front of the sensor 12 such that the body region to be scanned is visible in the acquired image. The user, such as a radiologist or technician, will then select a body region to be scanned, and the table 18 is moved to the desired start position without further corrections from the user. The images of patients often present a limited field of view based on a field of view (FOV) 19 of the sensor 12. Additional, different, or fewer actions may be performed. In one embodiment, the medical imaging system 10 will self-select a body region to be scanned.

FIG. 1 also shows one embodiment of a medical imaging system for estimating a 3D body surface of a patient and for estimating body regions of the patient. The medical imaging system 10 includes the sensor 12, processor 11, memory 13, medial scanner 14 and moveable patient table 18. The processor 11 and memory 13 may be part of the medical scanner 14, a computer, server, workstation, or other system for processing medical images from a scan of a patient. A workstation or computer without the medical scanner 14 may be used as the medical imaging system 10. The medical imaging system 10 includes the sensor 12 for capturing a sequence of surface images of the patient and the moveable patient table 18 for automatically positioning the patient 16.

Additional, different, or fewer components may be provided. For example, a computer network is included for remote image generation of locally captured surface images or for local image generation from remotely captured surface images. The machine-learned network is applied as a standalone application on the workstation or a local device or as a service deployed on network (cloud) architecture. As another example, a user input device (e.g., keyboard, buttons, sliders, dials, trackball, mouse, or other device) is provided for user alteration or placement of one or more body markers.

The sensor 12 may be a camera or a depth sensor, LIDAR, 2.5D, RGBD, stereoscopic optical sensor, or other depth sensor. One sensor 12 is shown, but multiple sensors may be used. A light projector may be provided. The sensor 12 may directly measure depth. The sensor 12 may include a separate processor for determining depth measurements from images, or the processor 11 determines the depth measurements from images captured by the sensor 12. The depth may be relative to the sensor 12 and/or a bed or table 18.

The sensor 12 is directed to the patient 16. The sensor 12 may be part of or connected to the medical scanner 14 or is separate from the medical scanner 14.

The processor 11 is a control processor, general processor, digital signal processor, three-dimensional data processor, graphics processing unit, application specific integrated circuit, field programmable gate array, digital circuit, analog circuit, combinations thereof, or other now known or later developed device for processing surface images. The processor 11 is a single device, a plurality of devices, or a network. For more than one device, parallel or sequential division of processing may be used. Different devices making up the processor 11 may perform different functions, such as applying the machine-learned network and configuring the medical scanner 14. In one embodiment, the processor 11 is a control processor or other processor of a medical diagnostic imaging system, such as the medical scanner 14. The processor 11 operates pursuant to and is configured by stored instructions, hardware, and/or firmware to perform various acts described herein.

The processor 11 is configured to train a machine learning architecture. Based on a user provided or other source of the network architecture and training data, the processor 11 learns features for encoders, decoders, discriminators, or other network parts to train the neural network. The result of the training is a machine-learned network or networks for estimating 3D body surfaces or body regions of a patient.

Alternatively, or additionally, the processor 11 is configured to apply one or more machine-learned networks. For example, an image-to-image or other neural network is applied to surface images from the sensor 12. The machine-learned neural network is applied to surface information. Based on the previous training, the network predicts the 3D body surfaces or body regions of a patient in response to application of the surface images. The network may receive depth information for the outside of the patient as inputs. The neural network may output 3D surface coordinates or probability maps (e.g., Gaussian heatmaps).

The processor 12 is configured to determine an isocenter of the patient based on the estimated 3D body surface of the patient. The processor 12 is also configured to generate an image. The output from the neural network may be an image, spatial distribution of landmarks, and/or a heat map. Annotations or graphics, such as for the landmarks, may be added to the image.

The medical imaging system 10 may optionally include a display, such as a CRT, LCD, projector, plasma, printer, tablet, smart phone or other now known or later developed display device for displaying the output, such as an image of the landmarks, or Gaussian heatmap. The display displays a medical image of body regions generated from the surface images.

The sensor measurements, 3D body surfaces, surface images, images of body regions, Gaussian heatmaps, network definition, features, machine-learned network, landmark images, output 3D surface coordinates, output landmark locations, and/or other information are stored in a non-transitory computer readable memory, such as the memory 13. The memory 13 is an external storage device, RAM, ROM, database, and/or a local memory (e.g., solid state drive or hard drive). The same or different non-transitory computer readable media may be used for the instructions and other data. The memory 13 may be implemented using a database management system (DBMS) and residing on a memory, such as a hard disk, RAM, or removable media. Alternatively, the memory 13 is internal to the processor 11 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 13). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The medical scanner 14 is a medical diagnostic imaging system configured to scan an internal region of a patient and generate anatomical information from the scan. The medical scanner 14 is a CT, MR, PET, SPECT, X-ray, or ultrasound scanner.

The medical scanner 14 is configured to generate anatomical information. The configuration uses settings for one or more parameters, such as an X-ray source voltage, table position and/or range of movement, gantry position and/or range of movement, focus, field of view, scan density, detector thresholds, transmission sequence, image processing settings, filtering settings, or image generation settings. Based on 3D body surfaces or body regions estimated from the surface images rather than scanning by the medical scanner 14, one or more settings of the medical scanner 14 are set. The patient 16 is imaged by the medical scanner 14 using the settings.

Figure 2:
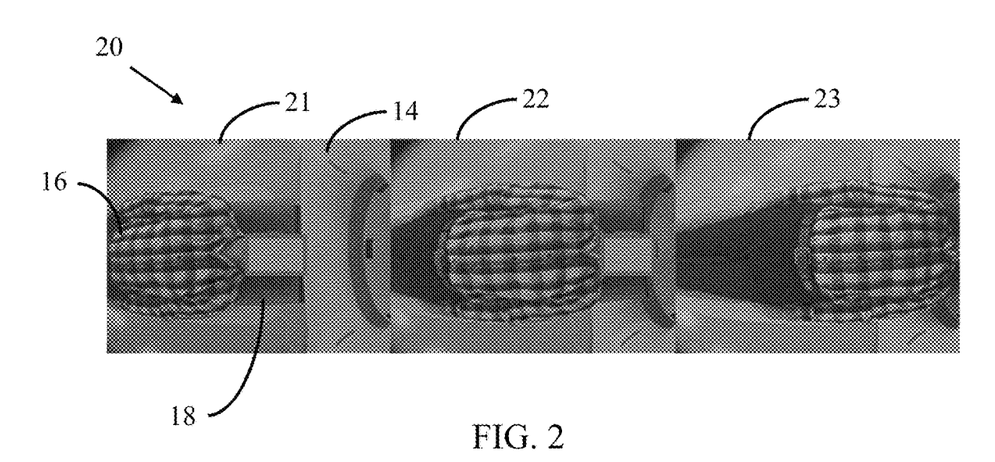
FIG. 2 shows an example sequence of images captured by the sensor of FIG. 1.

FIG. 2 shows a sample sequence of images 20 captured by the sensor 12 of FIG. 1. For example, the first image 21 in the sequence of images 20 shows a patient 16 lying on a patient table 18 outside and immediately adjacent to the scanner gantry 14. The second image 22 in the sequence of images 20 shows the patient 16 being moved by the patient table 18 in a direction towards the inside of the scanner gantry 14. The third image 23 in the sequence of images 20 shows the patient 16 partially inside the scanner gantry 14. Additional, different, or fewer images may be captured. In one embodiment, a single image is captured.

These example images 20 show the truncation and limited field of view of the patient 16 by the sensor 12. For example, in the initial image 21, the FOV 19 of the sensor 12 only allows the patient 16 to be visible from the patient's 16 head to the patient's 16 waist given the positioning of the patient 16. In the last example image 23, the patient 16 is visible from the patient's 16 neck to the patient's 16 knees. However, the patient's 16 head is unseen, as the head is outside the FOV 19 of the sensor 12. In another example, parts of a patient's 16 body may be unseen when those parts are within the FOV 19 of the sensor 12, but hidden or obstructed by parts of a medical imaging device, such as the scanner gantry 14.

Body markers are estimated from the images, and a 3D surface of a patient body is reconstructed. The estimation and reconstruction are from 2D images of a sequence by integrating temporal information into a body marker regression network. The 3D surface of the patient's body may be for the full patient body or part of the patient body. The obtained 3D surface can be directly used to regress a patient isocenter for patient centering and positioning. One exemplary method has three modules: (1) estimating dense body markers and reconstructing partial 3D surfaces of a patient body from a single frame, (2) building an extended FOV of the 3D surface of the patient body using a recurrent model, and (3) regressing a patient isocenter based on the reconstructed patient body surface and a patient table position. Additional, different, or fewer modules may be provided. The raw images captured by a 2D camera may be distorted to a certain extent. To accurately estimate body markers and a 3D surface of a patient, the images may be undistorted as a preprocessing step before being input into a machine learning algorithm.

Another exemplary method described herein solves the problem of limited field of views by estimating body regions of a patient and generating a heatmap that represents visible and unseen body region boundaries of the patient from 2D images of a video sequence by utilizing a temporal model in conjunction with a fully convolutional network. This approach has of two modules: (1) extrapolating unseen patient body regions to predict the body regions from each image with limited field of view and (2) temporal modeling to form spatiotemporal reasoning for body region detection from 2D camera stream. Additional, different, or fewer modules may be provided.

Figure 3:
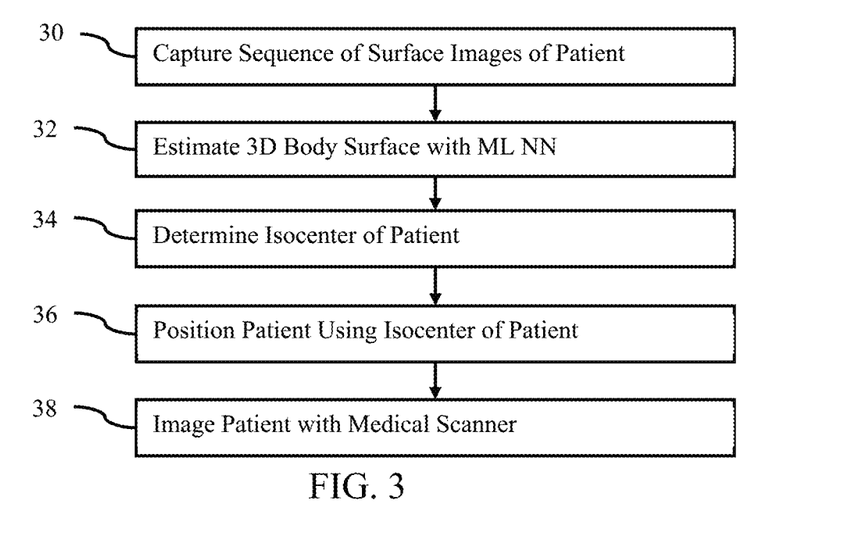
FIG. 3 is a flow chart diagram of one embodiment of a method for estimating 3D body surface of a patient located on a moveable patient table in a medical imaging system.

FIG. 3 is a flow chart diagram of one embodiment of a method for estimating a 3D body surface of a patient located on a moveable patient table in a medical imaging system. A machine-learned network is used to estimate a 3D surface of a patient. An isocenter of the patient is determined based on the estimated 3D body surface of the patient and based on a position of a moveable patient table. The estimated 3D body surface is reconstructed based on estimated body markers. The patient is then positioned via the moveable patient table based on the isocenter of the patient.

Rather than being a surface, the body markers are points or small volumes or areas representing a given anatomical landmark or body portion. A probabilistic distribution for a region may be used to indicate the location of a body marker (e.g., Gaussian distribution). The positions of any number of anatomical body markers may be estimated. Different body markers may be estimated for different purposes, such as for different applications or type of scanning in a same imaging mode (e.g., CT) or for different types of imaging modes (e.g., CT vs. ultrasound vs. MR).

The method of FIG. 3 is performed in the order shown (e.g., top to bottom or numerical), but other orders may be used. In alternative embodiments, these acts may occur in a different sequential order and/or one or more of these acts may occur substantially contemporaneously. Additional, different or fewer acts may be provided. For example, act 38 is not provided. In another example, act 34 is not provided as the estimated 3D body surface of the patient is used to position the patient without determining an isocenter of the patient.

In act 30, a sensor captures a sequence of surface images of a patient. In one example, the sequence of surface images may be a series of images arranged in a particular order, such as a successive order of at least two or more images (e.g., 2D video stream). In another example, the sequence of images may be a plurality of images, or at least two images, that are not arranged in a chronological sequence.

The sensor is directed at a patient. The sensor captures a sequence of images of the outer surface of the patient from one or more perspectives. Any portion of the outer surface may be captured, such as the entire patient from head to toe and hand to hand on one side or just the torso. The sensor captures the outer surface with the patient in a particular position, such as capturing a front facing surface as the patient lies in a bed or on a table. The sensor captures the surface images as red-green-blue (RGB) images.

The placement of one or more sensors (i.e., cameras) in the medical image scanning room (e.g., a CT scanning room, a PET scanning room, a MR scanning room, and/or the like) may be determined empirically in order to achieve optimal performance of the analytics. Various factors that may impact performance include, for example, the ease and/or expense of sensor installation, patient visibility constraints (e.g., the quality of the obtainable data), and sensor noise characteristics. There may be a trade-off between one or more of these factors. For example, with structured-light devices and time-of-flight devices, noise tends to increase as distance from the sensor increases. Depending on wavelength, noise may also increase in close proximity to the sensor. Sensor noise characteristics may be balanced against the field of view of the sensor when determining placement of a sensor. If a sensor is positioned too far away from the patient, there may be too much noise. If a sensor is positioned too close to the patient, the field of view may be too limited resulting in more unseen body portions, or body region boundaries, of the patient.

The outer surface is the skin of the patient. In other embodiments, the outer surface includes clothing. The sensor may use a frequency that passes through clothing and detects skin surface. In one example, the outer surface is captured as an image or photograph of the outside of the patient. In another example, the outer surface is captured as depths from the sensor to different locations on the patient. The sensor outputs the sensed image and/or depths.

In act 32, a processor estimates the 3D body surface of the patient. The captured surface images with or without other data are input to a machine-learned network and 3D surface coordinate values for the estimated 3D body surface are output. For example, surface images 22, 23 of the sequence of surface images 20 are input to the machine-learned network, which outputs a distribution of surface coordinates. The surface coordinates may be U,V coordinates based on a U,V mapping coordinate system. The processor applies the machine-learned network for 3D body surface estimation. Any inputs for which the network is trained to use are applied as an input feature vector, such as just the surface images. The outputs are points for locations. Alternatively, a Gaussian or other distribution representing a probability of location for each surface coordinate is output, such as outputting a heat map.

The estimating of the 3D body surface of the patient in act 32 of FIG. 3 includes estimating dense pose from single frames, or images, from the sequence of images 20. Dense human pose estimation aims at mapping all human pixels of an RGB image to the 3D surface of the human body. Given a sequence of 2D images 20 of the patient 16 lying on the table 18, a 3D surface is able to be estimated for a patient 16 for each image. For example, the first step of estimating dense pose, or a 3D surface, may involve estimating dense body markers for a first surface image of the sequence of surface images. The first surface image corresponds to a first imaged body portion of the patient. The second step may involve reconstructing a first 3D partial body surface for the first imaged body portion of the patient based on the first surface image.

Figure 4:
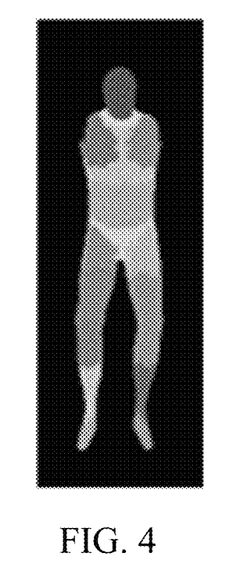
FIG. 4 illustrates an example of body part partitioning.

For surface-based representation of a human body, it is advantageous to break the body into multiple independent pieces and parametrize each piece using a local two-dimensional coordinate system such as UV mapping, which identifies the position of any node on this surface part. FIG. 4 shows an example of such body part partitioning into body parts. For example, a first body part may be a head. In another example, a second body part may be a neck or shoulder. The number of body parts in the body partitioning may be any number. In one example, the number of body parts after partitioning is 24. In another example, the number of body parts is customized to a different number, such as 16.

Each imaged body portion includes one or more body parts. In one example, the first imaged body portion includes just the patient's head. In another example, the first imaged body portion includes the patient's head, neck, shoulders, and torso. In one embodiment, the first imaged body portion of the patient and the second imaged body portion of the patient overlap. Once a first surface image that corresponds to a first imaged body portion is received, or captured, the first surface image may be partitioned into a plurality of parts. The plurality of parts corresponds to different body parts of the first imaged body portion. In some cases, after the partitioning described above, a resultant body part may be further partitioned. In the example above where the first imaged body portion includes the head, neck, shoulders, and torso of the patient, which corresponds to a first surface image of the patient, the first imaged body portion may be partitioned into a plurality of parts (e.g., head, neck, shoulders, and torso), where each part corresponds to a different part of the first imaged body portion. Each part of the plurality of parts includes a plurality of pixels, which are used to reconstruct a 3D partial body surface, as further described below.

To obtain image-to-surface correspondence in order to obtain 3D surface coordinates, a fully convolutional network (FCN) with an encoder and decoder is employed for dense pose estimation in conjunction with joint body part classification and surface coordinate regression. To reconstruct a first 3D partial body surface, a first surface image is partitioned into a plurality of parts. Then, applying the dense pose estimation network (i.e., FCN) to the first surface image, each pixel of the plurality of pixels for each part of the plurality of parts of the first surface image is classified as either a background class or a body part class. The body part class is a classification that corresponds to the different body parts of the first imaged body portion of the patient. The background class corresponds to additional extraneous or non-patient imaging data (e.g., environmental data representing at least a portion of the clinical setting, a technician, patient clothing, part of the gantry, part of the floor, part of the patient table, and/or the like). Next, a regressor predicts the exact 3D surface coordinates for each pixel within each body part.

Figure 5:
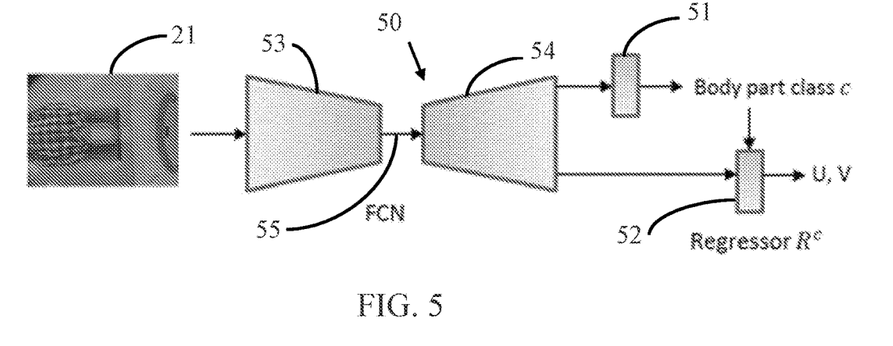
FIG. 5 illustrates an example network design for estimating a 3D body surface.

FIG. 5 illustrates an example network design for estimating a 3D body surface. A first surface image 21 is input into the FCN 50. Next, as described above, a classifier 51 assigns a part class $C_1$ or background class for each pixel of the RGB image (i.e., first surface image). Then, at least one regressor $R^C$ 52 determines 3D surface coordinates for each pixel by placing the pixel point in the continuous U, V coordinates parametrization of body part C. The network 50 includes an encoder 53 (convolutional) and decoder 54 (transposed-convolutional) with a bottleneck connection 55 between passing features at a greatest level of compression or abstractness from the encoder 53 to the decoder 54. The bottleneck connection 55 passes features from the encoder 53 to the decoder 54. Additional skip connections between the encoder 53 and decoder 54 at other scales may be used. In one embodiment, a plurality of regressors 52 are used where each of the plurality of regressors 52 corresponds to one of the parts of the plurality of parts of the first surface image 21. Each regressor 52 is separately or jointly trained for each part, which provides 3D coordinates within its respective part. The output of the FCN 50 is the estimated 3D body surface for each partial portion of the patient 16 that corresponds to the first surface image 21. This process is repeated for other surface images resulting in a 3D body surface for the patient.

The machine-learned network may be an image-to-image network trained to convert surface images to an image of locations of body markers, such as the body partitions shown in FIG. 4. For example, the trained convolution units, weights, links, and/or other characteristics of the network are applied to the surface images and/or derived feature values to extract the corresponding features through a plurality of layers and output the body markers. The features of the input images are extracted from the images. Other more abstract features may be extracted from those extracted features by the network. Depending on the number and/or arrangement of units or layers, other features are extracted from the input.

For training the machine-learned network, the machine learning network arrangement is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning.

For an image-to-image network, any machine training architecture for outputting a spatial distribution from an input spatial distribution may be used, such as a neural network. For example, U-Net or other fully convolutional network is used. A convolutional-to-transposed-convolutional network is used. One segment of layers or units applies convolution to increase abstractness or compression. The most abstract feature values are then output to another segment at a skip or bottleneck connection. The other segment of layers or units then applies transposed-convolution to decrease abstractness or compression, resulting in outputting the body markers or indication of class membership by location. FIG. 5 shows an example fully convolutional network 50, but other networks may be used. Any now known or later developed U-Net or image-to-image architectures may be used. Other fully convolutional networks may be used.

The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit.

A fully connected layer (e.g., dense layer) may be at the bottleneck of the network (i.e., between the encoder 53 and decoder 54 at a most abstract level of layers). The fully connected layer may make sure as much information as possible is encoded. Batch normalization may be added to stabilize the training.

Rather than pre-programming the features and trying to relate the features to attributes, the deep architecture (i.e. neural network) is defined to learn the features at different levels of abstraction based on an input image with or without pre-processing. The features are learned to reconstruct lower level features (i.e., features at a more abstract or compressed level). For example, features for reconstructing an image are learned. For a next unit, features for reconstructing the features of the previous unit are learned, providing more abstraction.

For training any of the networks, any number of samples in the training data may be used. For example, 1000 training examples with 100 for testing and 100 for validation are used. Various optimizers may be used, such as Adadelta, SGD, RMSprop, or Adam. The weights of the network are randomly initialized, but another initialization may be used. End-to-end training is performed, but one or more features may be set. Batch normalization, dropout, and data augmentation may be used. During the optimization, the different distinguishing features are learned. The 3D body surfaces given input surface images are learned.

The machine-learned network is trained to estimate 3D body surfaces for any number of surface images. The output is a 3D body surface of a patient having 3D position coordinates for the different pixels of the different body parts. The 3D surface is a mesh, but a fit template body may be used in other embodiments. The different body parts may be labeled. The 3D surface without body part labels may be output.

Once trained, the network may be applied to estimate 3D body surfaces from input surface images. The many samples in the training data (e.g., surface images and ground truth locations of body markers) are used to learn to output the 3D coordinates of the 3D body surface. The machine learning model is trained to learn the correspondence between the surface images and the 3D coordinates of the pixels of the surface images.

Once the 3D surface coordinates for pixels have been determined for one or more parts in the first imaged body portion, a 3D partial body surface for the first imaged body portion of the patient may be reconstructed. However, this only provides a 3D surface for a portion of the patient—the body portion corresponding to the first surface image (i.e., the first imaged body portion). Due to the limited field of view of the sensor 12, the 3D body surface is only reconstructed for a partial patient body. In one embodiment, the 3D body surface of the patient may be estimated on a synthesized image of an extended field of view of the patient. However, image synthesis is time-consuming and may require different workflows than desired. This embodiment also lacks the ability to obtain live surface reconstruction. In a second, preferred embodiment, a recurrent neural network with Long Short-Term Memory (LSTM) units is integrated with a dense body marker estimation network to enable 3D body surface estimation of a more complete body of a patient from a 2D video stream. The recurrent dense body marker detection network can be trained in an end-to-end manner. LSTMs may be used for 3D reconstruction of 2D images. A similar approach may be used for solving dense pose estimation for extended field of views. LSTMs may be leveraged to retain previous observations and incrementally refine the output of the network (i.e., 3D surface reconstruction) as more observations become available (i.e., applying the network to a sequence of surface images). LSTMs track the feature space of image sequences and reconstruct the surface model progressively.

Figure 6:
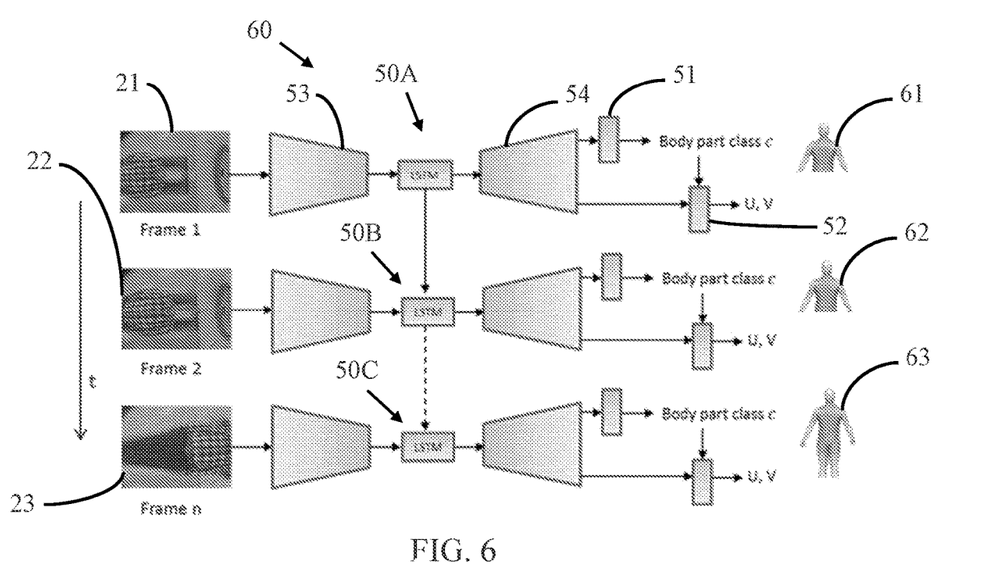
FIG. 6 illustrates an example recurrent network for body marker estimation applied to a 2D video sequence.

FIG. 6 illustrates an example recurrent network 60 applied to a 2D video sequence. The network 60 of FIG. 6 includes FCNs 50A, 50B, 50C, which are the same FCNs as FCN 50 of FIG. 5, discussed above, at different time intervals corresponding to different image frames. LSTMs are integrated into the FCNs 50A, 50B, 50C. The FCNs 50A, 50B, 50C are trained in an end-to-end manner. Otherwise, the function and components of FCNs 50A, 50B, 50C are the same as discussed above with regard to FCN 50 of FIG. 5. For sake of simplicity, the classifier 51, regressor 52, encoder 53, and decoder 54 have only been shown for FCN 50A. However, FCNs 50B and 50C also contain these components.

As discussed above with reference to FIG. 5, a first surface image 21 associated with a first imaged body portion is input into FCN 50A, which partitions the first surface image 21 into a plurality of parts, where the plurality of parts corresponds to different body parts of the first imaged body portion of the patient 16. Next, as described above, a classifier 51 assigns a part class $C_1$ or background class for each pixel of the first surface image 21. Then, at least one regressor $R^C$ 52 determines 3D surface coordinates for each pixel by placing the pixel point in the continuous U, V coordinates parametrization of body part C. The output of FCN 50A is a first 3D partial body surface 61 for the first imaged body portion of the patient 16 based on the first surface image 21.

This process is repeated for iterative surface images 22, 23, etc. The sequence of surface images may be a chronological sequence of images of the patient 16 as the patient 16 is moved into the scan gantry 14 by the patient table 18. For example, a second surface image 22 is input into FCN 50B in order to estimate a 3D body surface for the second surface image 22. The second surface image 22 corresponds to a second imaged body portion of the patient 16. FCN 50B partitions the second surface image 22 into a plurality of parts, where the plurality of parts corresponds to different body parts of the second imaged body portion of the patient 16. Another classifier 51 assigns a part class $C_1$ or background class for each pixel of the second surface image 22. At least one other regressor 52 determines 3D surface coordinates for each pixel by placing each pixel point in the continuous U, V coordinates parametrization of the second imaged body portion. The output of FCN 50B is a second 3D partial body surface for the second imaged body portion of the patient 16 based on the second surface image 22. The second partial body surface is combined with the previously output first 3D partial body surface 61 to get an aggregate, or more complete, 3D body surface 62.

Any number of surface images 20 may be input into the network 60. In the example shown in FIG. 6, three surface images 21, 22, 23 are used. Similar to the steps discussed above for surface images 21, 22, a third surface image 23 is input into FCN 50C in order to estimate a 3D body surface for the third surface image 23. The third surface image 23 corresponds to a third imaged body portion of the patient 16. FCN 50C partitions the third surface image 23 into a plurality of parts, where the plurality of parts corresponds to different body parts of the third imaged body portion of the patient 16. Another classifier 51 assigns a part class $C_1$ or background class for each pixel of the third surface image 23. At least one other regressor 52 determines 3D surface coordinates for each pixel by placing each pixel point in the continuous U, V coordinates parametrization of the third imaged body portion. The output of FCN 50C is a third 3D partial body surface for the third imaged body portion of the patient 16 based on the third surface image 23. As can be seen in FIG. 6, after three surface images 21, 22, 23 are input into the network 60, an even more complete 3D body surface 63 of the patient is obtained by aggregating the previously output first 3D partial body surface 61 and second 3D partial body surface.

To complete the reconstruction of the 3D body surface of the patient, a recurrent model integrated into the FCNs shown in FIG. 6 is used to reconstruct the 3D body surface of the patient from at least the first 3D partial body surface 61 and the second 3D partial body surface. The recurrent model may use any number of 3D partial body surfaces to reconstruct the 3D body surface of the patient. As discussed above, the recurrent model is a recurrent neural network comprising Long Short-Term Memory (LSTM) units that was trained end-to-end.

In act 34 of FIG. 1, an isocenter of the patient is determined based on the estimated 3D body surface of the patient and based on a position of the moveable patient table. The isocenter of the patient can be directly regressed from the 3D body surface of the patient and the table position. The isocenter may be regressed using any regression method. In one example, the isocenter may be regressed using a linear regression method. In another embodiment, the isocenter may be regressed using a non-linear regression method. In yet another embodiment, the isocenter may be regressed using a neural network. The determination of the isocenter of the patient can be performed for each target body region to be scanned. In one example, if the imaging target is a patient's head and the imaged body portion includes only the patient's head, an isocenter for the patient's head is determined. In another example, the imaging target may be the patient's abdomen area and the corresponding imaged body portion may include the patient's pelvic area, abdomen area, and mid-torso area. In this case, an isocenter is determined for the imaged body portion (i.e., pelvic area, abdomen area, and mid-torso area). The two isocenters of the preceding examples are different, since each deal with a different target body region to be scanned.

In act 36 of FIG. 1, the patient is positioned via the moveable patient table based on the determined isocenter of the patient. Once the isocenter of the patient is determined, the patient table can be moved accordingly and the patient can be properly positioned, thus enabling automatic isocentering. The isocenter of the patient or a part of the patient with a position known relative to the patient isocenter is aligned with an isocenter of the medical imager. The patient bed moves the patient relative to the isocenter of the medical imager based on the isocenter of the patient or part of the patient.

In a separate act not shown in FIG. 1, the processor may configure the medical scanner based on the estimated 3D body surface of the patient and/or the determined isocenter of the patient. The medical scanner may configure itself. The medical scanner is configured to scan with a field of view and/or other settings for the part of the patient positioned for imaging and/or the body surface. The scan range, focus, field of view, and/or other imaging parameters are based on the estimated 3D body surfaces and/or the determined patient isocenter. Alternatively, the user manually configures the medical scanner based on the estimated 3D body surface of the patient and/or the determined isocenter of the patient by entry with one or more controls.

In act 38, the medical scanner scans the patient. The patient is imaged. The imaging may be performed based on the configuration of the medical scanner. The resulting image from the scanning more likely shows the region of interest. Ionizing radiation from the scanning may be limited based on the configuration using the estimated 3D body surfaces and the determined patient isocenter.

Figure 7:
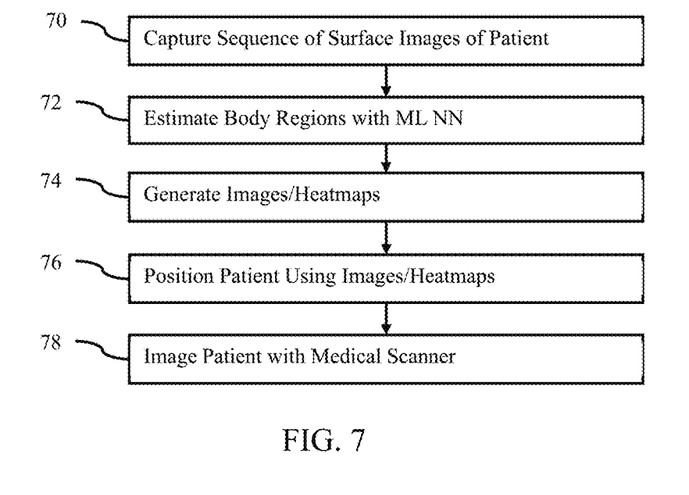
FIG. 7 is a flow chart diagram of one embodiment of a method for estimating body regions of a patient located on a moveable patient table in a medical imaging system.

FIG. 7 is a flow chart diagram of one embodiment of a method for estimating body regions of a patient located on a moveable patient table in a medical imaging system. A machine-learned network is used to estimate body regions of a patient. Estimated body regions are determined based on detected visible body region boundaries and extrapolated unseen body region boundaries of the patient. A body region boundary is a plane or line separating other parts, or body regions. The planes of the boundaries may be orthogonal to the longitudinal axis of the patient and bed. Body region boundaries of a patient may include a boundary at a headtop, neck, shoulder, hip, groin, knee, or ankle. An image, or heatmap, of the patient is generated by the machine-learned network in response to input of the surface images to the machine-learned network.

The method of FIG. 7 is performed in the order shown (e.g., top to bottom or numerical), but other orders may be used. Additional, different or fewer acts may be provided. For example, acts 76 and 78 are not provided. Moreover, in alternative embodiments, these acts may occur in a different sequential order and/or one or more of these acts may occur substantially contemporaneously.

In act 70, a sensor captures a sequence of surface images of a patient. In one example, the sequence of surface images may be a series of images arranged in a particular order, such as a successive order of at least two or more images (e.g., 2D video stream). In another example, the sequence of images may be a plurality of images, or at least two images, that are not arranged in a chronological sequence.

In act 72, a processor estimates the body regions of the patient. The captured surface images with or without other data are input to a machine-learned network and images, or heatmaps, showing body region boundaries for an extended view are output. For example, surface images 22, 23 of the sequence of surface images 20 are input to the machine-learned network, which outputs an extended view image or heatmap depicting body region boundaries (boundaries at the headtop, neck, shoulder, hip, groin, knee and ankle). The heatmap may be a Gaussian heatmap. The processor applies the machine-learned network for body region estimation. Any inputs for which the network is trained to use are applied as an input feature vector, such as just the surface images. The outputs are points for locations. Alternatively, a Gaussian or other distribution representing a probability of location for each surface coordinate is output, such as outputting a heat map.

In one embodiment, the estimating of the body regions of the patient in act 72 of FIG. 7 includes body region boundary detection from surface images with limited field of view and the extrapolation of unseen body regions from the visible body image. For each image, a trained network detects visible body region boundaries and extrapolates unseen boundaries. By including the unseen boundaries, the output of the detection contains a more complete set of the patient body region boundaries (boundaries at the headtop, neck, shoulder, hip, groin, knee and ankle). A machine-learned network, such as a fully convolutional network architecture, is employed to regress both visible and unseen body regions boundaries. These visible and unseen body region boundaries are represented as Gaussian heatmaps along the table longitudinal axis peaked at groundtruth location. The output of this exemplary method will be all the heatmaps on extended image.

Figure 8:
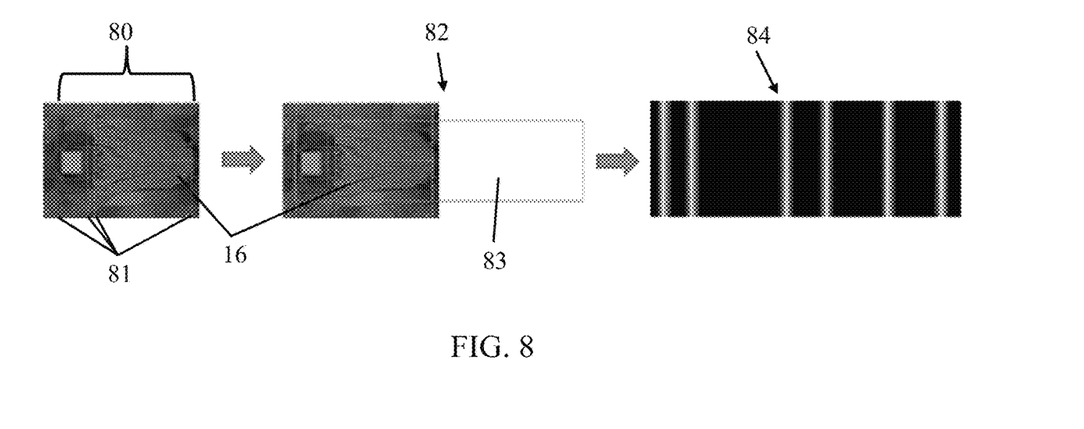
FIG. 8 illustrates one embodiment of the method of FIG. 7.

FIG. 8 illustrates one embodiment of the method of FIG. 7. Specifically, FIG. 8 shows an example of the method of estimating body regions 80 of a patient 16 and generating heatmaps 84 that represent visible body region boundaries 81 and unseen body region boundaries 83. In the example of FIG. 8, the planes of the boundaries are orthogonal to the longitudinal axis of the patient and bed. In a first step, visible body region boundaries 81 of the patient 16 are detected form the sequence of surface images 20 of the patient 16. In the example shown in FIG. 8, there are three body regions 80 and four visible body region boundaries 81 shown in the surface images of the patient 16. In a second step, unseen body region boundaries 83 of the patient 16 are extrapolated 82 based on the detected visible body region boundaries 81. In one embodiment, the second step may be performed simultaneously with the first step. Next, a temporal module is used to aggregate the detected visible body region boundaries 81 and the extrapolated 82 unseen body region boundaries 83 from the sequence of surface images. The result is an extended image containing heatmaps 84 that show both the detected visible body region boundaries 81 and the extrapolated 82 unseen body region boundaries 83. Based on this image containing heatmaps 84, the body regions of the patient for an extended view are determined. In the example shown in FIG. 8, there are seven distinct heatmaps 84. However, this number of heatmaps could be different, such as 5 total heatmaps 84.

Given a sequence of 2D images of a patient lying on a table, the temporal module can aggregate the body region detections from consecutive frames of the sequence of images. This can be modeled using recurrent networks such as Long Short-Term Memory (LSTM) units, similar to previously discussed methods.

Figure 9:
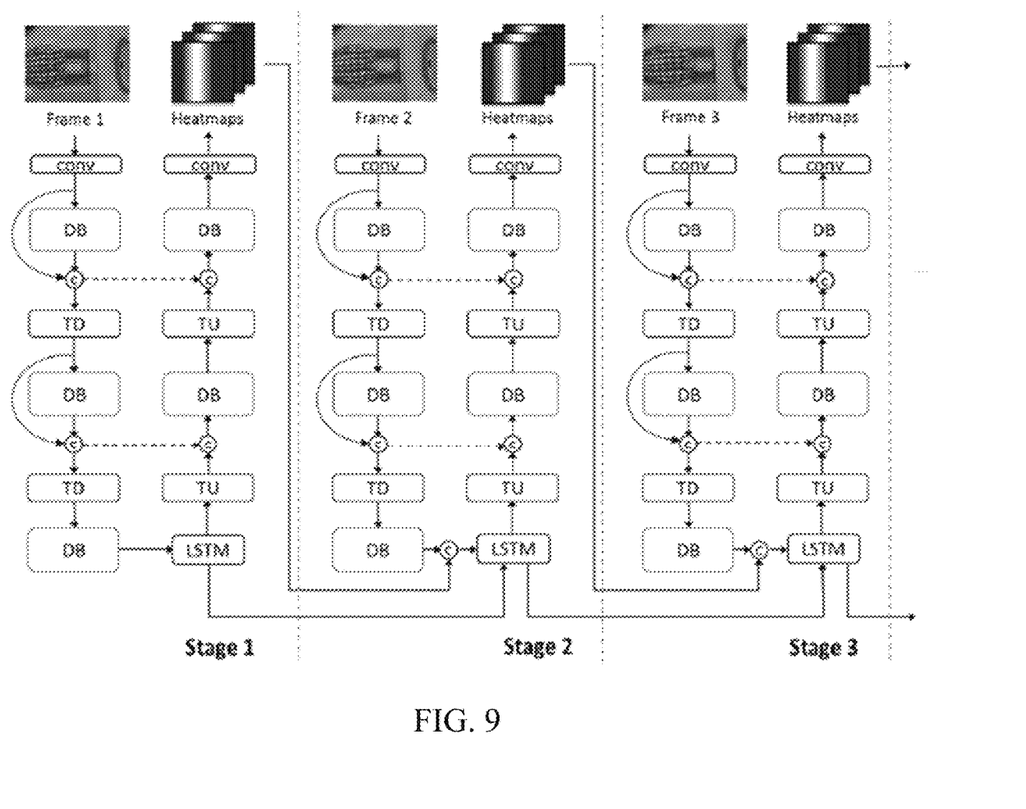
FIG. 9 illustrates an exemplary recurrent patient body region estimation network applied to a 2D video sequence.

One exemplary network is illustrated in FIG. 9. FIG. 9 illustrates an exemplary recurrent network applied to a 2D video sequence. Note that for illustration purposes, only 2 Downsample/Upsample operations are utilized. The following terms are used in FIG. 9: "Cony" for Convolution Layer, "DB" for DenseBlock, "TD" for TransitionDown, "TU" for TransitionUp, "c" for Concatenate, "LSTM" for Convolutional LSTM, and "--->" for Skip Connection. FIG. 9 illustrates multi-frame modelling where features are capable of being shared across stages. This network is built upon fully convolutional DenseNet but adapted for a sequential regression task. In FIG. 9, each convolution layer in DenseBlock is densely connected, i.e., features are reused in consecutive layers. In this embodiment, the architecture of the network can be customized to meet the performance requirement on accuracy and runtime speed. For example, DenseBlock can be used with a growth rate of k=12, with 3 dense layers in each dense block, and four Downsample/Upsample modules to ensure a large enough receptive field. Downsample modules are completed by a MaxPool operation and Upsample modules consists of stride transposed convolution followed by a center crop method.

As shown in FIG. 9, the network consists of T stages, where T is the number of frames. In this example, three stages are shown. In each stage, one frame (i.e., image) from a sequence of images will be sent into the network as input. The downsampling path is responsible for extracting coarse semantic features, followed by an upsampling path that recovers the input image resolution at the output. Transition Down is composed of BN, followed by ReLU, a 1×1 convolution, dropout with p=0.2 and a non-overlapping max pooling of size 2×2. TransitionUp is composed of a 3×3 transposed convolutions with stride 2 to compensate for the pooling operation. The skip connections between the two paths aim to retain the information lost due to the downsampling operation. The extracted semantic features from downsampling path will be concatenated with the downsampled heatmaps from the previous stage, and they will be sent into a convolutional LSTM module. Outputs from LSTM will pass an upsampling path to produce heatmaps for each frame. LSTM enables weight sharing of all the layers across stages, which reduces the number of parameters in the network. LSTMs have been used for post-processing, which is suboptimal and making training difficult since LSTMs process high dimensional flattened heatmaps. However, in the proposed embodiment the convolutional LSTMs process low-dimensional latent features and can be learned jointly in an end-to-end manner.

In act 74, the processor generates images or heatmaps by the machine-learned network in response to input of the surface images to the machine-learned network. The heatmaps, such as Gaussian heatmaps, represent visible and unseen body region boundaries of the patient along a longitudinal axis of the moveable patient bed.

In act 76, the patient is positioned via the moveable patient table based on the generated images or heatmaps. Once the images or heatmaps are generated, the patient table can be moved accordingly and the patient can be properly positioned, thus enabling automatic patient positioning. The patient is positioned so that the desired body part is in the field of view of the medical scanner.

In a separate act not shown in FIG. 7, the processor may configure the medical scanner based on the estimated body regions of the patient and/or the generated images/heatmaps. The medical scanner may configure itself. The medical scanner is configured to scan with a field of view and/or other settings for the part of the patient positioned for imaging and/or the body surface. The scan range, focus, field of view, and/or other imaging parameters are based on the estimated body regions and/or the generated images/heatmaps. Alternatively, the user manually configures the medical scanner based on the estimated body regions of the patient and/or the generated images/heatmaps by entry with one or more controls.

In act 78, the medical scanner scans the patient. The patient is imaged. The imaging may be performed based on the configuration of the medical scanner. The scan range, focus, field of view, and/or other imaging parameters are based on the estimated body regions of the patient and/or the generated images/heatmaps. The resulting image from the scanning more likely shows the region of interest. Ionizing radiation from the scanning may be limited based on the configuration using the estimated body regions of the patient and/or the generated images/heatmaps.

The embodiments discussed above aim to obtain robust patient body regions from a 2D video stream with a limited field of view. The proposed method disclosed herein is able to predict both visible and unseen body region boundaries. By doing so, the proposed embodiment can achieve better performance due to more context and output structure, and because it enables easy temporal modeling. Predicting landmarks implicitly enforces global shape consistency between the body regions, which have the following benefits: (1) it allows approximate prediction of a bodyline even when it is not in field of view (using context), and (2) it enables efficient spatio-temporal integration of the body region information. These embodiments may also lead to an automated medical scanning workflow with a 2D/3D camera.

The estimation of 3D body surfaces, the determined patient isocenter, and the estimated body regions may assist in planning a medical scan. The 3D body surfaces, the determined patient isocenter, and/or the estimated body regions may be used to plan for scanning by any modality, such as CT, MR, fluoroscopy or ultrasound. For CT scanning, the 3D body surfaces, the determined patient isocenter, and the estimated body regions may be used to determine the scan range, depending upon which body part needs to be scanned and how accurately the nearby structures may be predicted. This may reduce the amount of ionizing radiation applied to the patient. The 3D body surfaces, the determined patient isocenter, and the estimated body regions may also assist in coil placement for MR scanning. For ultrasound scanning, the 3D body surfaces, the determined patient isocenter, and the estimated body regions may assist in probe guidance by providing approximate position. For fluoroscopy using dyna-CT scans, the 3D body surfaces, the determined patient isocenter, and the estimated body regions may be useful for positioning the patient and/or the scanner. Any setting or parameter of the medical scanner may be determined or configured based on the estimated 3D body surfaces, the determined patient isocenter, and the estimated body regions.

The sensors, or cameras, used for capturing the surface images of the patient are calibrated. Extrinsic calibration may be used. The extrinsic calibration is done through an external calibration target such as a checkerboard. First, the checkerboard is aligned to the gantry center by manually adjusting the table and checkerboard position to be aligned with the laser cross-hair emitted from the gantry. Then, the table is moved out of the gantry with a known distance so that the full checkerboard is inside the field of view of the camera. Then, the camera pose estimated from the checkerboard can be used to derive the extrinsic camera parameters by compensating the known table offset. As the table may not be perfectly aligned with the axes of the gantry, multiple measurements at different table positions may be needed in order to register the table axes with the gantry axes, such that the camera pose can be compensated with the rectified table offset according to the gantry axes. This is a time-consuming, expensive, and cumbersome calibration process.

One embodiment for solving the problem of extrinsic camera calibration involves using the scanner gantry itself for calibration, as opposed to using other external calibration targets. This embodiment applies to a ceiling mounted camera and gantry camera setups where the bore opening of the scanner gantry is partially visible in a field of view of the camera. The gantry from the scanner forms a perfect circle in 3D space. When the gantry is projected to a camera looking from an angle, the gantry forms an ellipse in the camera image. With a calibrated camera (where the focal lengths, principal point, and radial distortion parameters are known) and known circle size (the bore opening of the gantry), estimation of the relative pose of the camera with respect to the gantry with a single image is possible.

Figure 10:
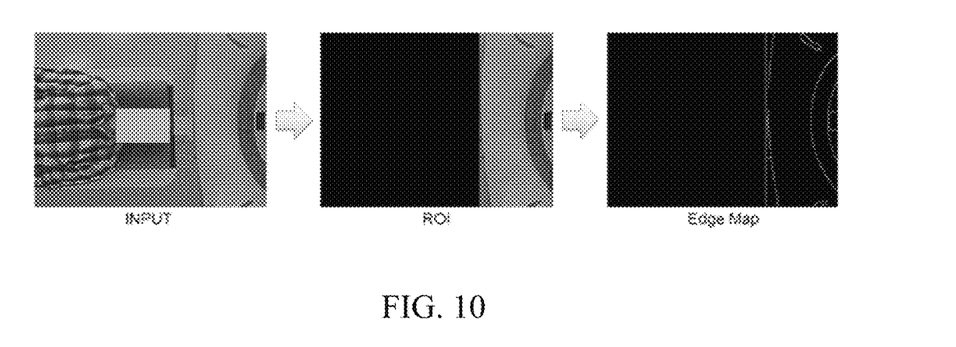
FIG. 10 is an example of image preprocessing for self-calibration of extrinsic camera parameters using a scanner gantry.

The workflow for an exemplary embodiment using an extrinsic camera contains 3 steps: (1) image preprocessing, (2) ellipse detection, and (3) camera pose estimation. In the first step, it is assumed that the region of interest (ROI) of the gantry in the image is given in advance. For example, in the gantry mount camera cases, the gantry is either inside the left ⅓ portion of the image or the right ⅓ portion depending how the camera is oriented. Within the ROI, general edge detection such as using a canny edge detector is performed on the image to get an edge map as shown in FIG. 10, which illustrates an example of image preprocessing when calibrating a camera using a scanner gantry.

Figure 11:
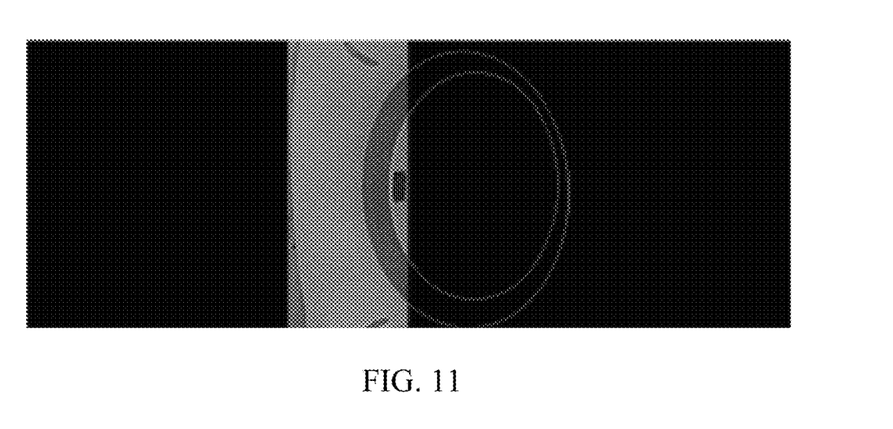
FIG. 11 shows an example of ellipse detection in self-calibration of extrinsic camera parameters using a scanner gantry.

With the edge map generated from the image preprocessing step, contours are detected that form an ellipse. As there is a very strong contrast on the boundary of the gray rim inside the gantry, the candidate contour can be easily traced along the nearby edge points. By sampling the points on the candidate contour, a 2D ellipse can be fit to each detected contour. FIG. 11 shows an example of ellipse detection where the image border is extended to show the full ellipses (shown at right) estimated from the contour points (shown at left) detected inside the original image.

Figure 12:
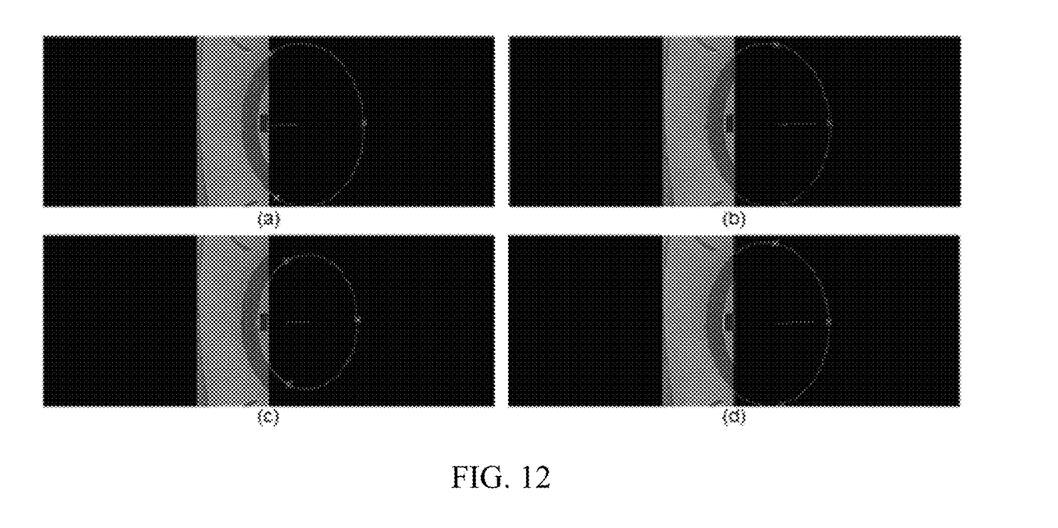
FIG. 12 shows estimated circle center and normal projected into an image in self-calibration of extrinsic camera parameters using a scanner gantry.

In the third step, the camera pose is estimated for each ellipse detected in the second step. The pose estimation algorithm is based on the camera calibration algorithm proposed by Chen et al. in "Camera Calibration with Two Arbitrary Coplanar Circles" (Proceedings of ECCV 2004). The algorithm estimates the extrinsic camera parameters and focal length of a camera by using one single image of two co-planar circles with arbitrary radius. The algorithm is not directly applicable to all use cases as the two circular rims of the gantry are not co-planar. However, the circle radius (e.g. the bore opening of the gantry) can be obtained from a scanner specification. In addition, the camera can be calibrated in advance to get the intrinsic parameters such as focal lengths, principal points, and radial distortion parameters. Therefore, one circle with known radius is sufficient to estimate the camera pose. FIG. 12 shows estimated circle center and normal projected into the image, where (a) and (b) are the two possible solutions for the left rim circle of the gantry and (c) and (d) are the two possible solutions for the right rim circle of the gantry.

Figure 13:
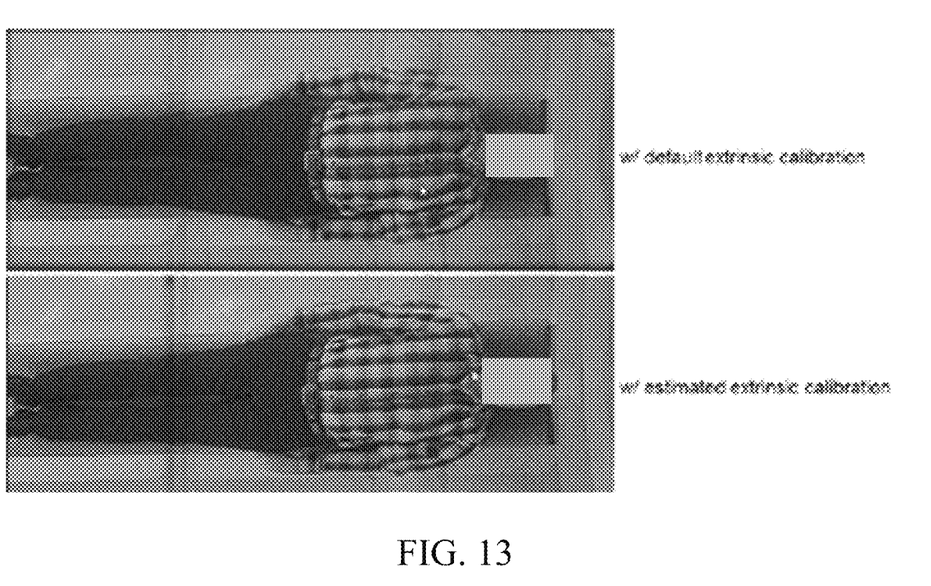
FIG. 13 illustrates an improvement of image stitching results using an exemplary calibration method.

Note that for each detected ellipse, there are two possible solutions as shown in FIG. 12. Since it is known that the contour inside the original points are located at the lower portion of the gantry, FIG. 12(a) and FIG. 12(c) are the solutions. Assuming the bore opening is 700 mm, the estimated camera pose in the above example has a rotation (0.0965, 1.9885, 92.7792)-degree in three axes and translation (455.74, −14.85, 734.99) mm. This is very close to the specification where ideally the translation is (457±5, 0, 735±5) mm and the rotation is (0.0, 0.0, 90.0)-degree. In order to verify the extrinsic calibration, a few images of a person may be stitched at different table positions. As can be seen from FIG. 13, the images are stitched much better by using the method proposed herein (bottom image) over the default, i.e., existing, method (top image).

Using the gantry directly as a calibration target is an improvement over the existing methods where an external calibration target is needed and manual alignment of the target to the gantry is also required. The proposed approach can also be used as an automatic health check feature to validate whether the camera position relative to the gantry has been deviated from the nominal position. Thus, it is useful not only for gantry-mounted 2D camera settings for the latest CT scanners, but also useful for ceiling-mounted 3D camera settings for CT or MR scanners.

One alternative method other than the proposed approach or the existing approach is to use scanner scanned data to register the camera pose. For this to work, one or more additional calibration targets are used. In a first step, 3D geometry of the calibration targets is reconstructed with a set of object images by moving the table. Then the calibration targets are scanned by the scanner to get volumetric reconstruction. The camera pose can be derived by the rigid transformation between the camera-reconstructed geometry and the scanner-reconstructed geometry. Although this method could have the highest accuracy as the volumetric reconstruction is involved, it may suffer from the imperfect camera-reconstructed geometry and it also requires additional targets which hinders its usage for the automatic health check feature.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

What is claimed is:

1. A method for estimating body regions of a patient located on a moveable patient table in a medical imaging system, the method comprising:
   capturing, with a sensor, a sequence of surface images of the patient;
   estimating, by a processor, the body regions of the patient by a machine-learned network in response to input of the surface images to the machine-learned network; and
   generating, by the processor, Gaussian heatmaps by the machine-learned network in response to input of the surface images to the machine-learned network, the Gaussian heatmaps representing visible body region boundaries and unseen body region boundaries of the patient along a longitudinal axis of the moveable patient table.

2. The method of claim 1 wherein estimating comprises estimating with the machine-learned network comprising a fully convolutional network.

3. The method of claim 1 wherein estimating further comprises:
   detecting visible body region boundaries of the patient from the sequence of surface images of the patient;
   extrapolating unseen body region boundaries of the patient based on the detected visible body region boundaries;
   aggregating, by a temporal module, the detected visible body region boundaries and the extrapolated unseen body region boundaries from the sequence of surface images; and
   determining the body regions of the patient based on the aggregated visible body region boundaries and the unseen body region boundaries.

4. The method of claim 3 wherein the temporal module comprises a recurrent neural network comprising LSTM units.

\* \* \* \* \*